"""
US009441050B2

(12) United States Patent
Hnasko et al.

(10) Patent No.: US 9,441,050 B2
(45) Date of Patent: Sep. 13, 2016

(54) HIGH-AFFINITY MONOCLONAL ANTI-PRION ANTIBODIES

(71) Applicants: The United States of America, as represented by the Secretary of Agriculture, Washington, DC (US); The Regents of the University of California, Oakland, CA (US)

(72) Inventors: Robert M Hnasko, Port Costa, CA (US); Larry Stanker, Livermore, CA (US); Stanley Prusiner, San Francisco, CA (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 80 days.

(21) Appl. No.: 13/949,905

(22) Filed: Jul. 24, 2013

(65) Prior Publication Data

US 2014/0065723 A1  Mar. 6, 2014

Related U.S. Application Data

(62) Division of application No. 13/157,216, filed on Jun. 9, 2011, now abandoned.

(60) Provisional application No. 61/353,480, filed on Jun. 10, 2010.

(51) Int. Cl.
| | |
|---|---|
| *C07K 16/18* | (2006.01) |
| *G01N 33/68* | (2006.01) |
| *C07K 16/44* | (2006.01) |
| *C07K 16/28* | (2006.01) |

(52) U.S. Cl.
CPC ............ *C07K 16/44* (2013.01); *C07K 16/2872* (2013.01); *G01N 33/68* (2013.01); *G01N 33/6896* (2013.01); *C07K 2317/33* (2013.01); *C07K 2317/34* (2013.01); *G01N 2500/02* (2013.01); *G01N 2800/2828* (2013.01)

(58) Field of Classification Search
CPC ............. G01N 33/68; G01N 33/6896; G01N 2500/02; G01N 2800/2828; C07K 16/2872; C07K 16/44; C07K 2317/34
USPC ................... 424/185.1; 436/501; 530/388.9
See application file for complete search history.

(56) References Cited

U.S. PATENT DOCUMENTS 7,344,842 B1 * 3/2008 Garssen et al. ............... 435/7.1

OTHER PUBLICATIONS

MABN780, Anti-PrP, clone DRM1-31 Antibody product sheet, EMD Millipore Corp. Retrieved from internet May 21, 2016.*
MABN768, Anti-PrP, clone DRM2-118 Antibody product sheet, EMD Millipore Corp. Retrieved from internet May 27, 2016.*
MABN772, Anti-PrP, clone DRM1-60 Antibody product sheet, EMD Millipore Corp. Retrieved from internet May 27, 2016.*
Stanker LH et al. Novel epitopes identified by anti-PrP monoclonal antibodies produced following immunization of Prnp o/o Balb/cJ mice with purified scrapie prions. Hybridoma, 2012, 31(5):314-324.*

* cited by examiner

*Primary Examiner* — Kimberly A. Ballard
(74) *Attorney, Agent, or Firm* — John D. Fado; Mark McNemar

(57) ABSTRACT

Peptide sequences that specifically bind infectious prion protein for the generation of antibodies and therapeutic agents are disclosed herein.

8 Claims, 16 Drawing Sheets

FIG. 5A

| Inoculum | ID$_{50}$ U/mL | Specific Infectivity (ID$_{50}$/mg) |
|---|---|---|
| PrP$^{Sc}$ Brain | 9.75 | 390 |
| PrP$^{Sc}$ DRM | 11.71 | 8674 |
| PrP$^{Sc}$ DRM PK PTA G100 | 13.46 | 16825 |

FIG. 5B

10% Crude Brain Homogenate
(PrP$^{Sc}$)
↓
Sucrose Gradient Centrifugation
↓
Detergent Resistant Membrane (DRM) Fraction
(PrP$^{Sc}$ DRM)
↓
Proteinase-K (PK) Treatment
(PrP$^{Sc}$ DRM-PK)
↓
Phosphotungstic Acid (PTA) Precipitation
↓ ↓
Pellet            Supernatant
(PrP$^{Sc}$ DRM-PK-PTA)
↓
Sephadex G100 Fractionation
↓
Void Fraction
(PrP$^{Sc}$ DRM-PK-PTA-G100)
↓
PTA Precipitation
↓ ↓
Purified PrP$^{Sc}$ Pellet            Supernatant
(PrP$^{Sc}$ DRM-PK-PTA-G100-PTA)
↓
Immunization (Mice)
↓ ↓
*Prnp$^{0/0}$* Balb c/J            Wild-type Balb c/J
↓ ↓
PrP$^{Sc}$ Positive            PrP$^{Sc}$ Negative
Antisera                        Antisera

FIG. 6

HIGH-AFFINITY MONOCLONAL ANTI-PRION ANTIBODIES

CROSS REFERENCE TO RELATED APPLICATIONS

This application is a divisional of application Ser. No. 13/157,216, filed Jun. 6, 2011, which claims priority to U.S. Provisional Patent Application Ser. No. 61/353,480 filed Jun. 10, 2010 herein incorporated by reference in its entirety.

FIELD OF THE INVENTION

The present invention relates to the enrichment and purification of prion proteins and the generation of antibodies to infectious prion proteins.

BACKGROUND OF THE INVENTION

Prion diseases are a family of progressive, fatal neurodegenerative disorders caused by the accumulation of the alternatively folded prion protein $PrP^{Sc}$. In the CNS, prions produce neuronal cell death, spongiform vacuolation and gliosis (1). The $PrP^{Sc}$ protein is extractable from diseased tissue and biochemically distinguished from endogenous $PrP^{C}$ by partial protease resistance and detergent insolubility (2). Both $PrP^{C}$ and $PrP^{Sc}$ share the same amino acid sequence, but $PrP^{Sc}$ adopts an abnormal conformation that is transmissible and serves as a template for the conversion of host $PrP^{C}$ into the pathogenic prion isoform (3;4). The mechanism responsible for the transmission, conformational conversion of $PrP^{C}$ to $PrP^{Sc}$, and subsequent disease progression remains enigmatic.

Detection of infectious prions relies on combined use of immunoassay and histopathological assessment of brain tissue from infected animals (5). Current immunoassays are dependant on antibodies that recognize both the normal and abnormal isoforms of PrP. To distinguish abnormal $PrP^{Sc}$ from normal $PrP^{C}$ requires limited digestion with proteinase-K (PK) to hydrolyze PK-sensitive $PrP^{C}$ while retaining the PK-resistant $PrP^{Sc}$ (PrP 27-30). The PrP 27-30 protein is smaller than $PrP^{C}$ and intact $PrP^{Sc}$ and thus can be recognized by a mobility shift following SDS-PAGE and Western blot detection with anti-PrP antibodies (6;7). Yet prion accumulation in the brain is progressive and infected, asymptomatic animals pose significant sampling challenges as minimal accumulation of $PrP^{Sc}$ is localized to other more accessible tissue or fluid compartments (8;9). Moreover, variability in the efficacy of prion proteolysis of samples confounds detection of low-level $PrP^{Sc}$ (10).

There remains an acute need for a sensitive and selective prion immunodiagnostic assay capable of pre-clinical assessment of infected animals from accessible tissues or fluids (11). Most immunoassay detection limits are insufficient to detect low-level prion contamination that can transmit disease by bioassay. Current assays are confounded by reliance on removal of PK-sensitive $PrP^{C}$ as no antibody has emerged that can selectively distinguish infectious $PrP^{Sc}$ from $PrP^{C}$ (12). The need to remove $PrP^{C}$ protein from samples often diminishes immunoassay sensitivity by reducing the amount of $PrP^{Sc}$ and increasing assay background. Moreover, the occurrence of PK-sensitive $PrP^{Sc}$ isoforms poses additional concerns for many immunodiagnostic assays (13).

The difficulty of prion antibody generation is underscored by the identical primary structure of normal and abnormal PrP protein isoforms and isolation of purified infectious prion. The use of synthetic PrP peptides or recombinant $PrP^{C}$ has been successful in generating anti-PrP antibodies for detection of both $PrP^{C}$ and $PrP^{Sc}$ proteins, but use of a $PrP^{C}$ derivative cannot yield an antibody that selectively bind the structurally distinct $PrP^{Sc}$ (14;15). Since the primary structure of $PrP^{Sc}$ is identical to PrP, a recombinant $PrP^{Sc}$ protein cannot be generated. Moreover, the $PrP^{C}$ antigen has proven to be a poor immunogen as endogenous $PrP^{C}$ protein negates a robust immune response (16;17). The immunogenicity of $PrP^{C}$ antigen has been improved by using Prnp-null mice ($Prnp^{0/0}$) with resulting production of high-affinity anti-PrP antibodies (14). However, the use of a $PrP^{C}$ antigen invariably leads to production of antibodies that recognize $PrP^{C}$ with a low probability of generating a $PrP^{Sc}$ selective antibody capable of directly discriminating between normal $PrP^{C}$ and infectious $PrP^{Sc}$.

The most common methods for the diagnostic confirmation of prion disease involve clinical assessment, followed by post-mortem histopathological evaluation of brain tissue along with biochemical detection of PrP 27-30 (21;22). Several problems have confounded the pre-clinical diagnostic detection of prion. First, accumulation of $PrP^{Sc}$ increases progressively over time; second, most $PrP^{Sc}$ resides in the brain which imposes biopsy challenges. Third, prion concentrations below current immunoassay detection limits can transmit disease in animal bioassay (23;24). Fourth, no direct detection method has been developed that can distinguish $PrP^{Sc}$ from $PrP^{C}$ without enzymatic or chemical manipulation to render endogenous $PrP^{C}$ undetectable while retaining $PrP^{Sc}$ activity. Indeed, no antibody has emerged that can selectively bind $PrP^{Sc}$ but not PrP, moreover, no surrogate analyte has been identified that can identify prions in preclinical animals (22;25). Finally, species and prion strain variability presents additional detection challenges as a result of distinct tissue distribution and availability (26; 27).

Useful biochemical methods have emerged for the enrichment of $PrP^{Sc}$ from brain homogenates that take advantage of differences in sedimentation and solubility (28;29). Yet, these preparative methods have proven insufficient to yield $PrP^{Sc}$ enriched fractions suitable for crystal formation or as immunogen for the generation of $PrP^{Sc}$ selective antibodies. Several factors likely contribute to the inability to generate a $PrP^{Sc}$ selective antibody. First, the choice and preparation of inoculum have favored the generation of $PrP^{C}$ antibodies. The use of recombinant $PrP^{C}$ invariably yields antibodies that recognize PrP. Moreover, preparation of a native $PrP^{Sc}$ is often confounded by contaminating proteins including PrP. Second, wt animals expressing endogenous $PrP^{C}$ may provide a less robust system for the generation of $PrP^{Sc}$ antibodies (30). Third, the method used for screening antibodies requires the selective discrimination of those that bind $PrP^{C}$ from those that bind $PrP^{Sc}$. A method that yields that yields abundant $PrP^{Sc}$ from diseased tissue and demonstrates a progressive increase in specific infectivity of prions and generation of high-titer antisera with selective activity to PrP is therefore desired.

SUMMARY OF THE INVENTION

Method for prion enrichment in biological tissue or fluids wherein the prion enriched samples serves as antigen for detection of prion proteins.

Method for purifying infectious prion protein from biological tissue and fluids wherein the purified prion serves as inoculum for antibody generation.

Method for generation and use of Prnp$^{o/o}$ Balbc/J and Balb/c Bailey mice.

Method of identifying hybridoma cells producing prion specific monoclonal antibodies.

Method of generating prion specific antisera and monoclonal antibodies against prion protein.

Mouse hybridoma cells and resultant high-affinity monoclonal anti-prion antibodies.

BRIEF DESCRIPTION OF THE DRAWINGS

FIGS. 1 A-C are graphs showing the isolation of prions from crude brain homogenate with detergent resistant membranes (DRM). Sucrose density gradient centrifugation separates lipid-associated proteins from the majority of brain proteins via differences in sucrose buoyancy at 4° C. Fractionation of the gradient (12×1 mL) resulted in detection of a small protein peak observed within the 5-30% sucrose zone (buoyant fractions #4-5), whereas the bulk of proteins from both PrPC and PrPSc brain homogenate were retained at the bottom of the gradient (FIG. 1A). Western blots revealed that the majority of detectable PrPC and PrPSc were localized to the lipid-rich DRM fractions #4-5 (FIG. 1B; top panels). Proteinase-K (+PK) digestion of the gradient fractions from PrPSc infected brain resulted in an expected molecular weight shift and detection of PrPSc in the DRM fractions (FIG. 1B; top right panel). The DRM protein marker Flotillin-1 served as a positive control to confirm the integrity of the gradient and localization of the DRM fractions (FIG. 1B; bottom panels). The majority of PrPC and proteinase-K resistant PrPSc were detected by ELISA in DRM fractions #4-5 (FIG. 1C).

FIGS. 2 A & B is a graph and Western blot of showing the enrichment of prions in detergent resistant membrane fractions (DRM). Increased detection of PrP 27-30 in DRM fraction (>40-fold) relative to crude brain homogenate by direct ELISA (FIG. 2A). Protein normalization by BCA (5 μg/mL); RLU=relative light units; quantitation of three independent samples (Mean±SEM; P=<0.001). Western blot comparison of detectable PrP 27-30 in crude hamster brain homogenates, DRM and phosphotungstic acid (PTA) precipitated DRM proteins (FIG. 2B). Progressive increase in detection of three PrPSc glycoforms in DRM fractions and PTA precipitated DRM fractions compared to crude brain homogenates. Protein normalization by BCA prior to PK-treatment and PTA precipitation.

FIG. 3 is a Western blot showing the molecular weight status of prion proteins in detergent resistant membrane (DRM) fractions. Western blot detection of PrPC following fractionation of normal brain DRM on a linear sucrose gradient showed detection of PrPC across a range of molecular weights composed primarily of mono- and di-glycosylated isoforms (FIG. 3; top left panel). The oligomeric status of PrPSc from Scrapie infected DRM differs from PrPC with the majority detected as high molecular weight (Fraction #12; >440 kDa) aggregate (FIG. 3; top right panel). This high molecular weight PrPSc species is composed primarily of mono- and di-glycosylated PrP with detection of non-glycosylated PrP across lower molecular weights (Fractions #3-10). Proteinase-K digestion of gradient fractions from Scrapie DRM shows that all the PK-resistant PrPSc is localized to fraction #12 as a high molecular weight aggregate whereas the non-glycosylated PrP in fractions #3-10 is PK-sensitive (FIG. 3; bottom right panel). Caveolin-1 (Cav-1) and flotillin-1 (Flot-1) are established DRM protein markers known to form high molecular weight oligomeric complexes and were used as positive controls to validate the integrity of the sucrose gradient (FIG. 3; middle and bottom left panels respectively). The linear sucrose gradient was calibrated with know molecular weight protein standards and their mobility and molecular weight are indicated by the large arrows at the bottom of FIG. 3.

FIG. 4 A-D are graphs and Western blots that shows the concentration and purification of prion by PTA and size exclusion chromatography. Enriched PrPSc DRM fractions were treated with proteinase-K then proteins PTA precipitated, the solubalized (PrPSc DRM-PK-PTA) material was then fractionated by size exclusion chromatography (Sephadex G100), Protein concentration of fractions was determined by BCA assay (FIG. 4A; solid line) and PrPSc detection by ELISA (FIG. 4A; dashed line). A small protein peak was observe in fraction #5 that corresponded to the void fraction of the column (proteins >100 kDa) which also contained the majority of detectable PrPSc. Western blot detection of G100 fractionated PrPSc DRM-PK-PTA-G100 showed a major band in the void fraction #5 (FIG. 4B). A second PTA protein precipitation following G100 fractionation recovered detectable PrPSc in the void fractions (FIG. 4C). Evaluation of the purified PrPSc DRM-PK-PTA-G100-PTA material by silver and Coomassie stain (FIG. 4D; left and middle panel respectively) showed detectable PrPSc protein at the expected molecular weight that corresponded to PrPSc detection by Western blot (FIG. 4D; right panel).

FIGS. 5 A & B is a plot and table showing a significant increase in specific infectivity with $PrP^{Sc}$ purification. Days of survival were determined by hamster bioassay for purified Scrapie brain homogenate preparations (FIG. 5A). Transmissible disease was observed following intracerebral inoculation of 1% PrPSc (25 μg), PrPSc DRM (1.35 μg), and PrPSc PK-treated PTA precipitated material fractionated by size exclusion on Sephadex G100 (PrPSc DRM-PK-PTA-G100; 0.8 μg). N=sample size. Comparison of ID50 and specific infectivity following intracerebral inoculation of 1% crude brain homogenate (brain), DRM, and purified prion (DRM-PK-PTA-G100) by incubation time assay (FIG. 5B). Isolation of PrPSc in DRMs from lipid rafts results in >20-fold, and purified PrPSc DRM-PK-PTA-G100>40-fold, increase in specific infectivity relative to crude brain.

FIG. 6 is a schematic diagram that outlines prion purification and immunization strategy. An outline of steps involved in prion purification from brain homogenate to immunization of Prnp0/0/Balbc/J and wild-type Balb/cJ mice with purified PrPSc (PrPSc DRM-PK-PTA-G100-PTA).

FIGS. 7 A & B are plots and Western blots showing detection of HaPrP (90-231) with antisera from prion immunized $Prnp^{0/0}$/Balb/cJ, but not wt Balb/cJ mice. Antisera from Prnp0/0/Balb/cJ mice detected SHaPrP (90-321) at dilutions >1:30K by direct binding ELISA; whereas antisera from immunized wt Balb/cJ mice failed to detect SHaPrP (90-231) at any dilution (FIG. 7A). Antisera from prion immunized Pmp0/0/Balb/cJ, but not wt mice, detected SHaPrP (90-231), Syrian hamster brain PrPC (Ha PrPSc DRM; no PK), and PrPSc (Ha PrPSc DRM; +PK) by Western blot (FIG. 7B). Detection of PK-resistant PrPSc was observed with antisera diluted >25K from two representative Prnp0/0/Balb/cJ (#1-2) and wt Balb/cJ (#3-4) mice immunized with purified prion antigen. RLU=relative light units.

FIG. 8 are Western blots comparing prion detection from infected hamster brain and DRM with antisera from $Prnp^{0/0}$/Balb/cJ mice immunized with purified $PrP^{Sc}$ to that of an established anti-prion antibody (IPC1). Western blot comparing binding of antisera from a prion immunized Prnp0/

0/Balb/cJ to normal and infectious hamster brain homogenate (30 µg/lane), recSHaPrP(90-231); 100 ng/lane), and normal and infectious hamster brain DRM (10 µg/lane) preparations (FIG. 8; top panel). Antisera detected PK-sensitive PrPC, recSHaPrP(90-231), and PK-insensitive PrPSc in brain homogenates and DRM preparations; no other protein bands were observed. A comparative Western blot showed similar binding of the monoclonal anti-prion antibody IPC1 to brain homogenate, recombinant PrP, and DRM preparations (FIG. 8; bottom panel) as antisera from Prnp0/0/Balb/cJ mice. PK=proteinase-K treatment (+). Protein normalization by BCA.

FIG. 9 A-F compares prion binding of three DRM monoclonal antibodies purified from cloned hybridomas generated from prion immunized Prnp0/0 Balbc/J mice. Al$^1$ DRM anti-prion selectively bind PrPC and PrPSc from hamster infected brain DRM fractions by ELISA (panels A,C,E) and Western blot (panels B,D,F).

FIG. 10 compares binding of five anti-prion monoclonal DRM antibodies to recombinant hamster (ha PrP90-231), mouse (Mo PrP 89-230), ovine (Ov PrP 23-231), and human (Hu PrP 90-231) PrP proteins by ELISA. All five DRM monoclonal antibodies recognize Ha PrP 90-231 with equal affinity, whereas DRM1-60-6-2 binds Ov PrP 23-231 and DRM2-118-9-4 binds Hu PrP 90-231, with strong affinity.

FIG. 11 compares binding of three unique anti-prion monoclonal DRM antibodies to endogenous brain PrP from multiple species by Western blot. DRM1-60 and DRM2-118 show broad species specificity whereas DRM1-31 shows strong binding to hamster (Ha) and cervid (Ce) only.

DETAILED DESCRIPTION OF THE INVENTION

Figure 1A:
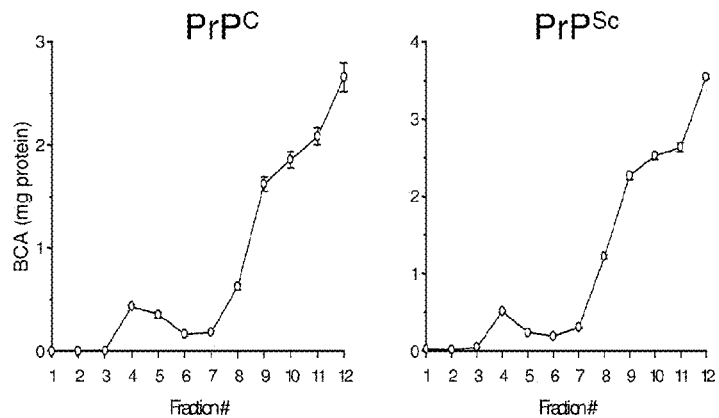
Figure 1B:
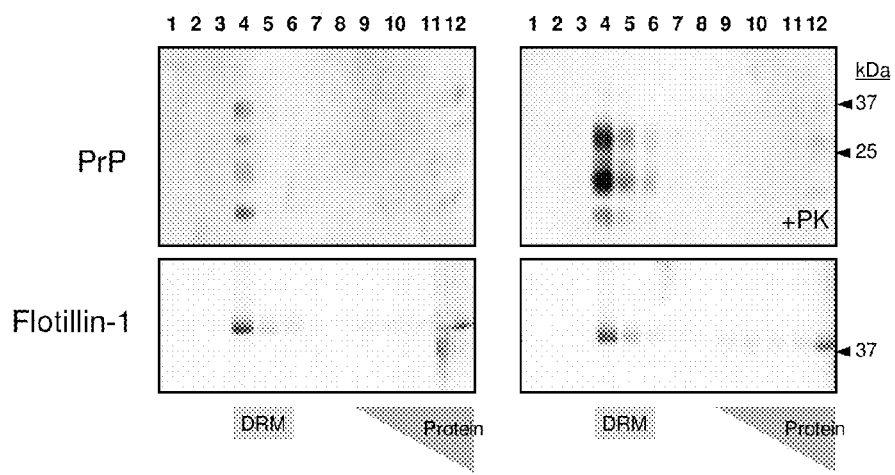
Figure 1C:
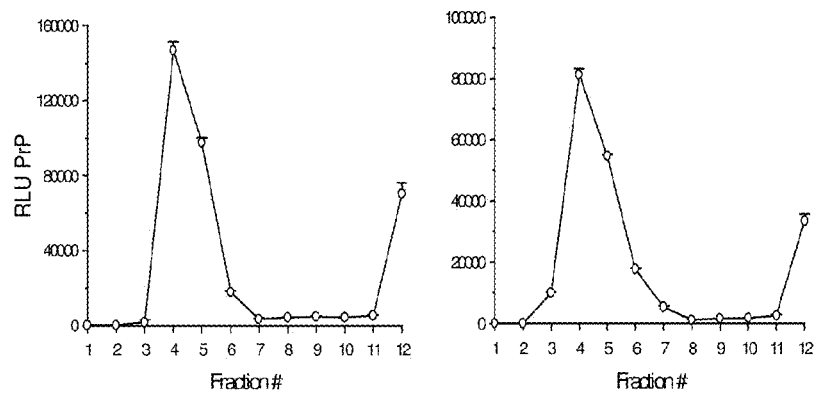
Figure 2A:
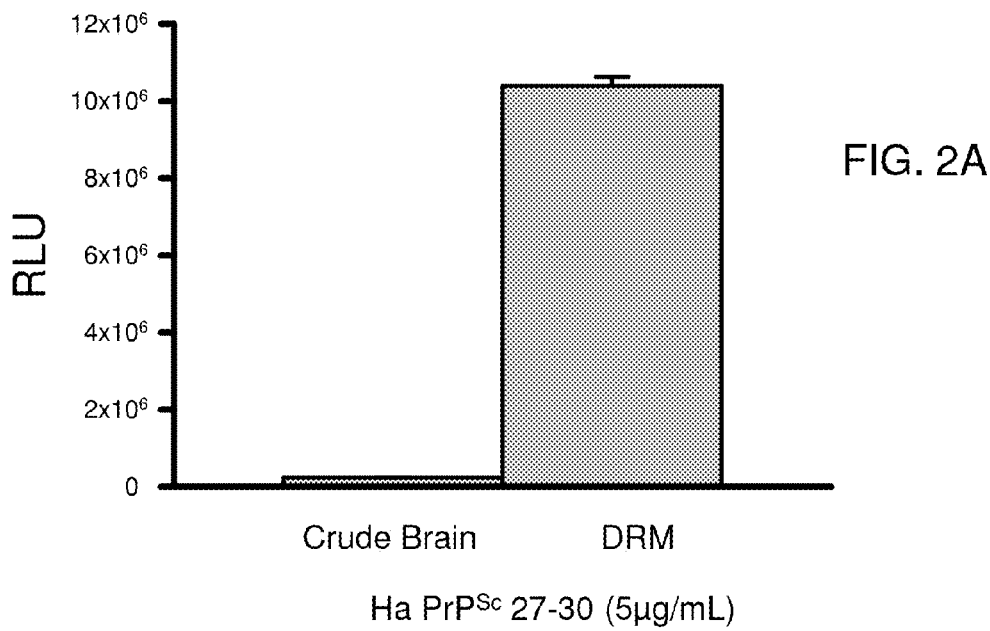
Figure 2B:
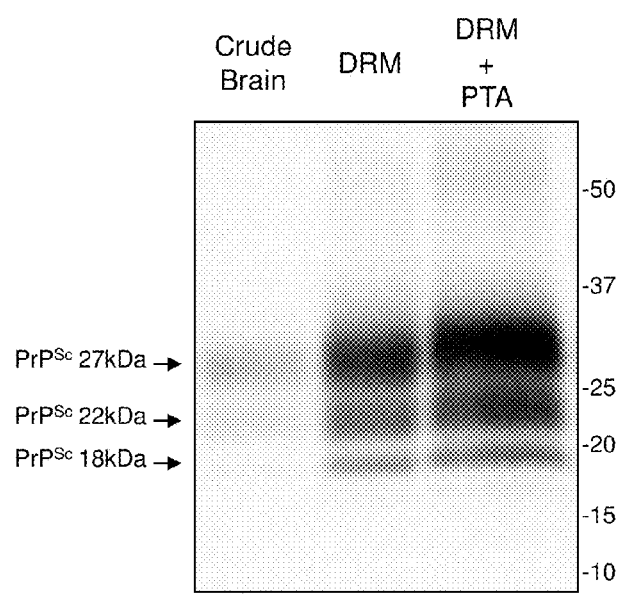
Figure 3:
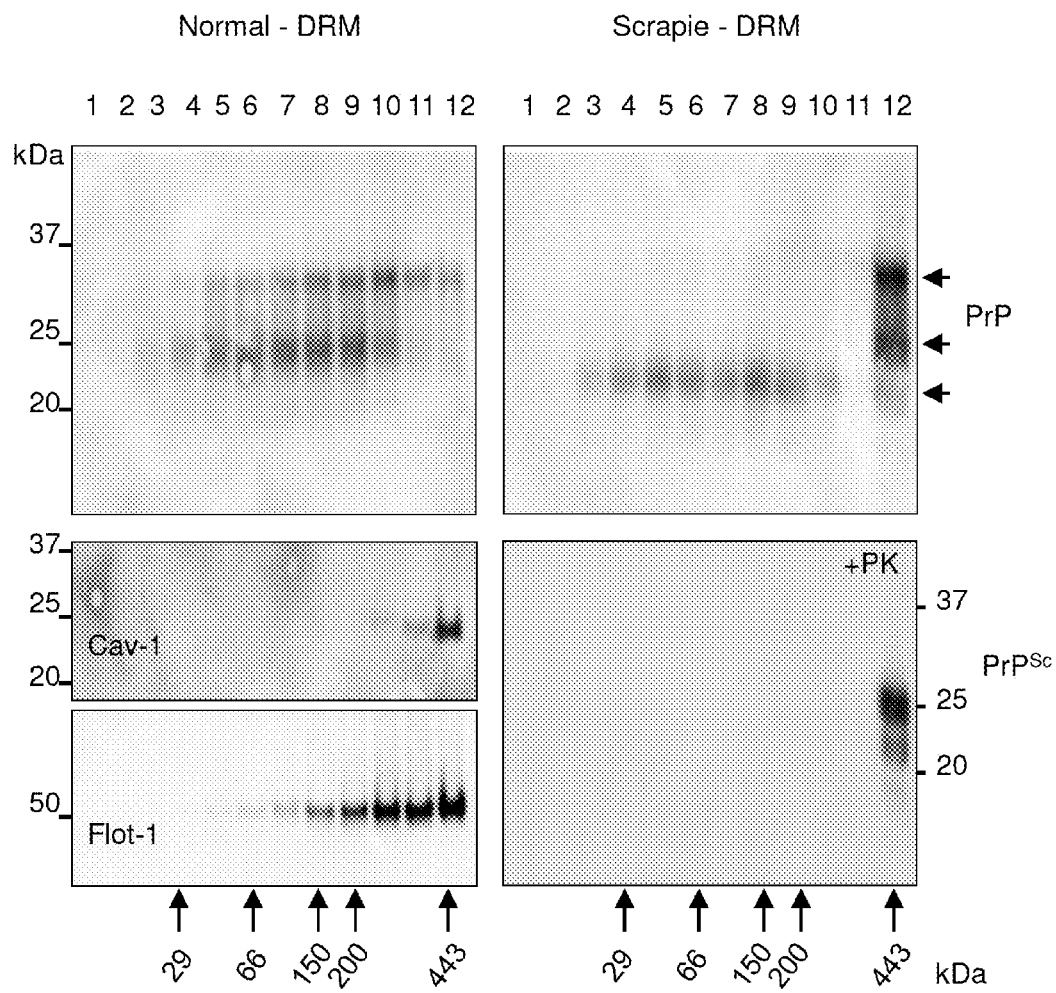
Figure 4A:
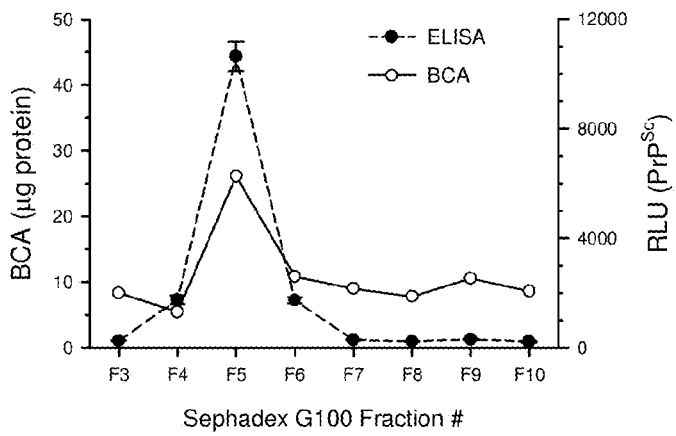
Figure 4B:
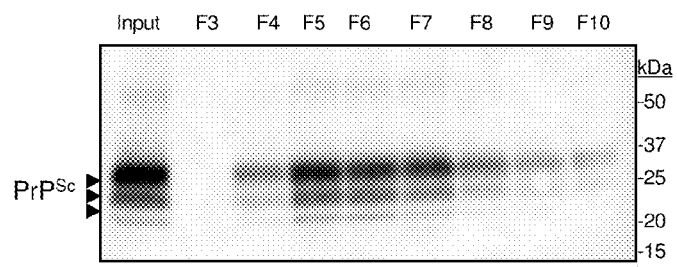
Figure 4C:
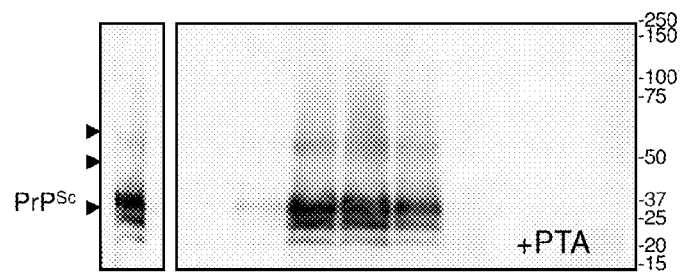
Figure 4D:
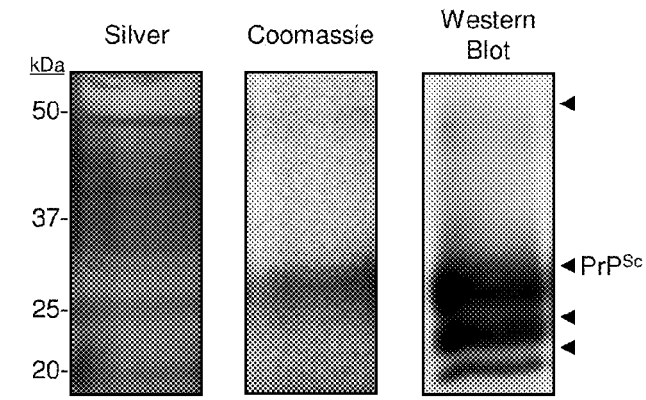
Figure 7A:
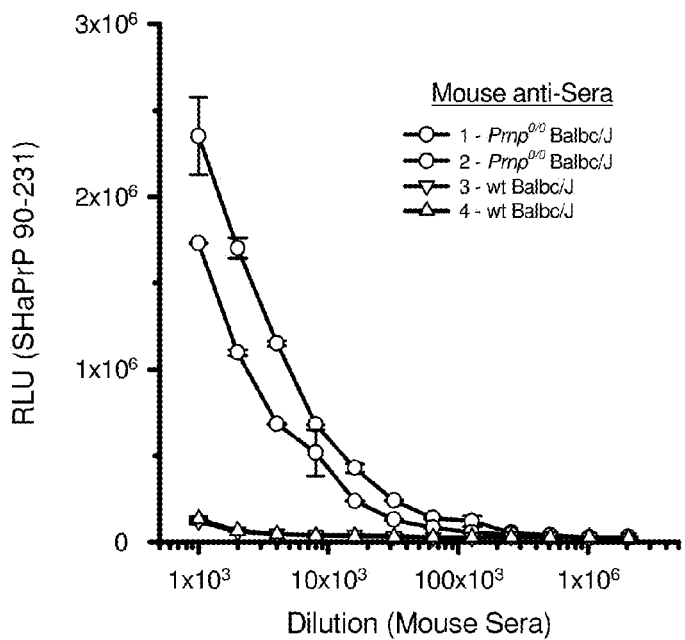
Figure 7B:
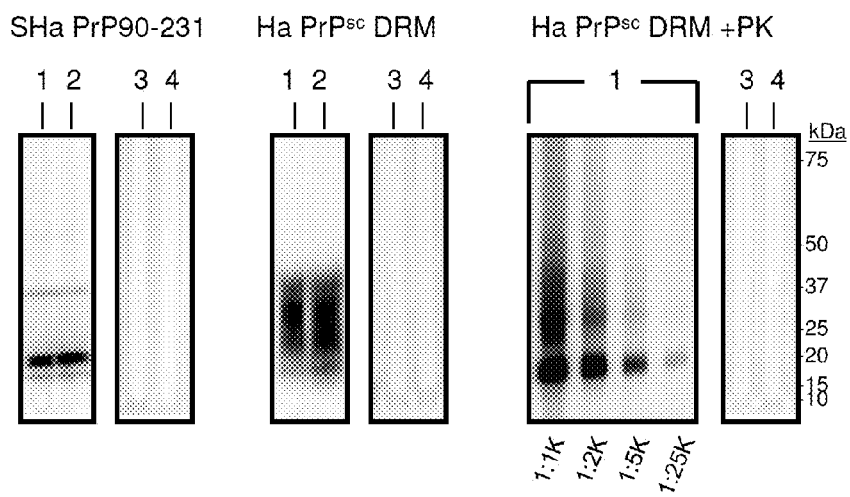
Figure 8:
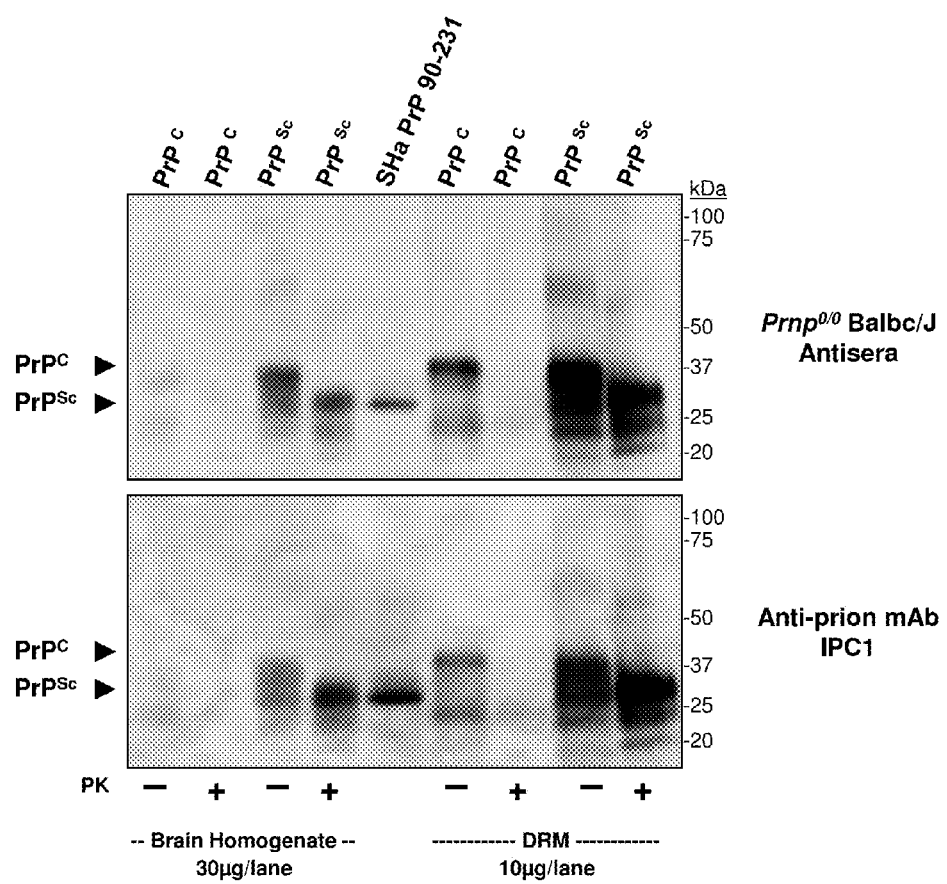
Figure 9A:
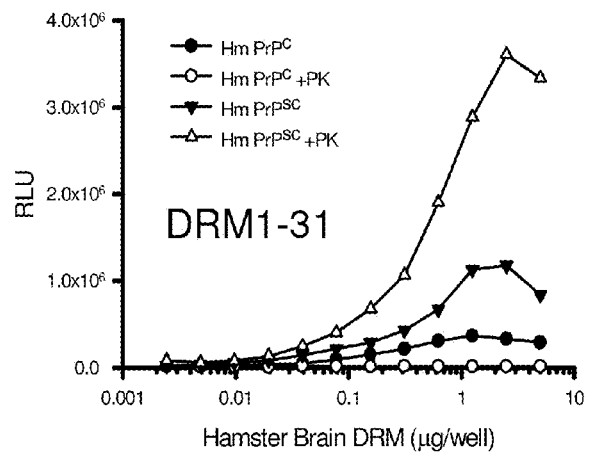
Figure 9B:
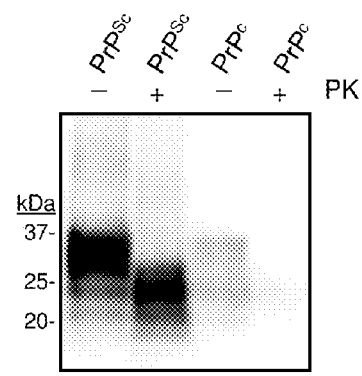
Figure 9C:
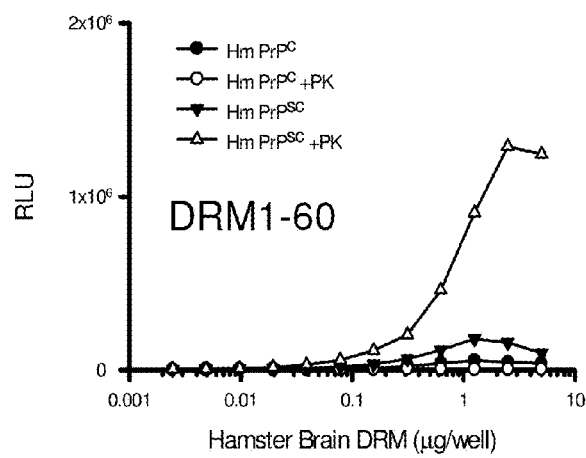
Figure 9D:
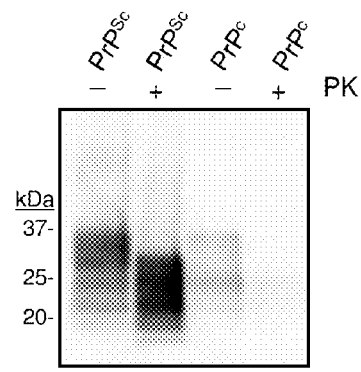
Figure 9E:
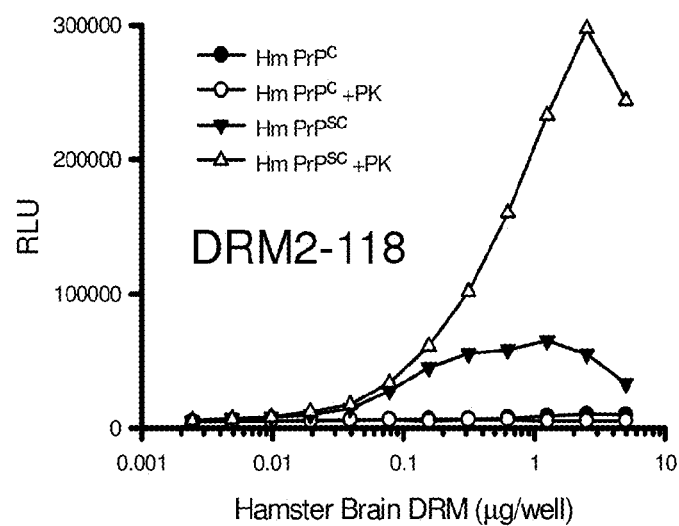
Figure 9F:
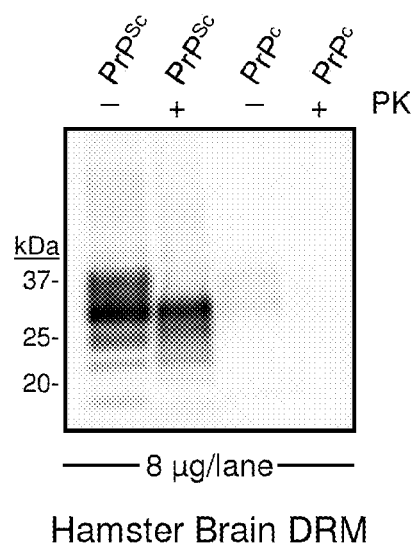
Figure 10:
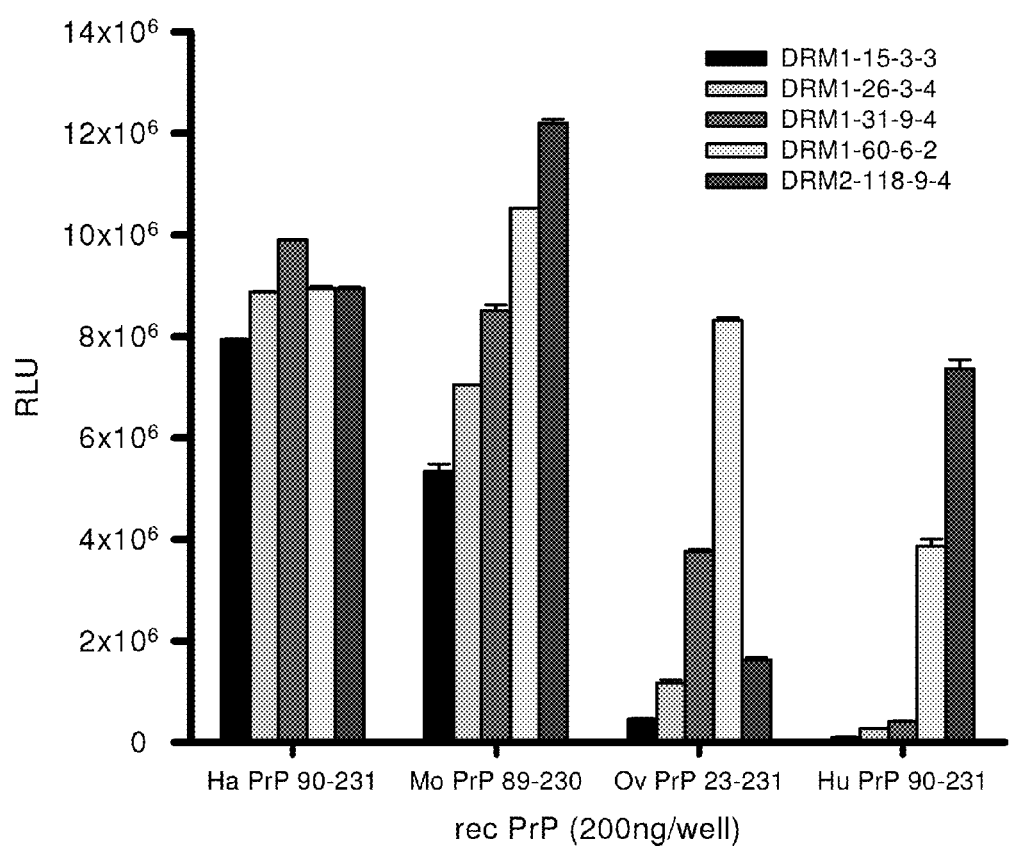
Figure 11:
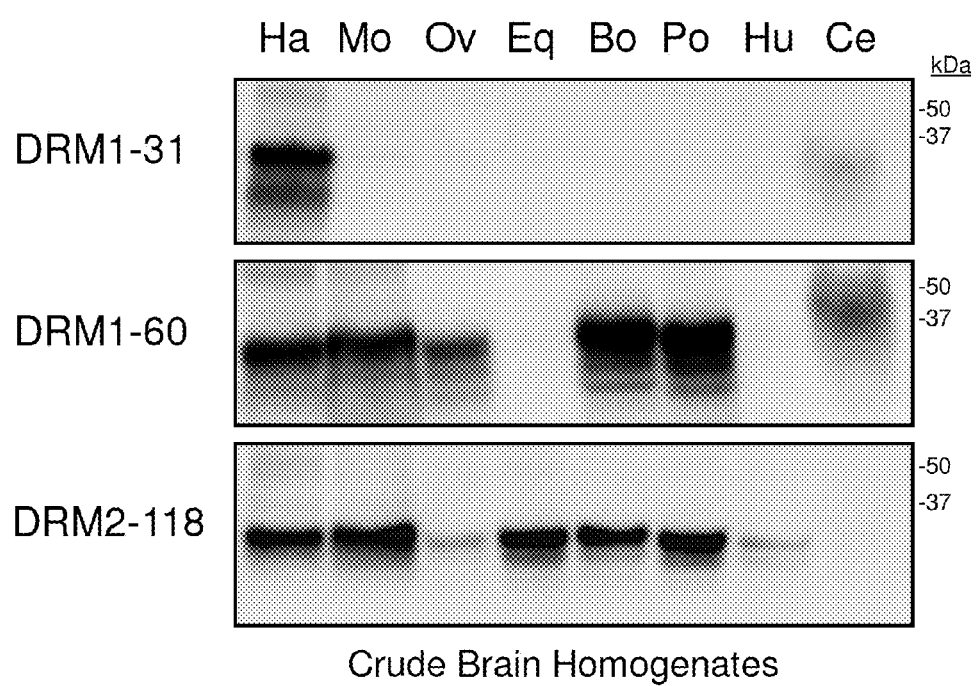
Figure 12:
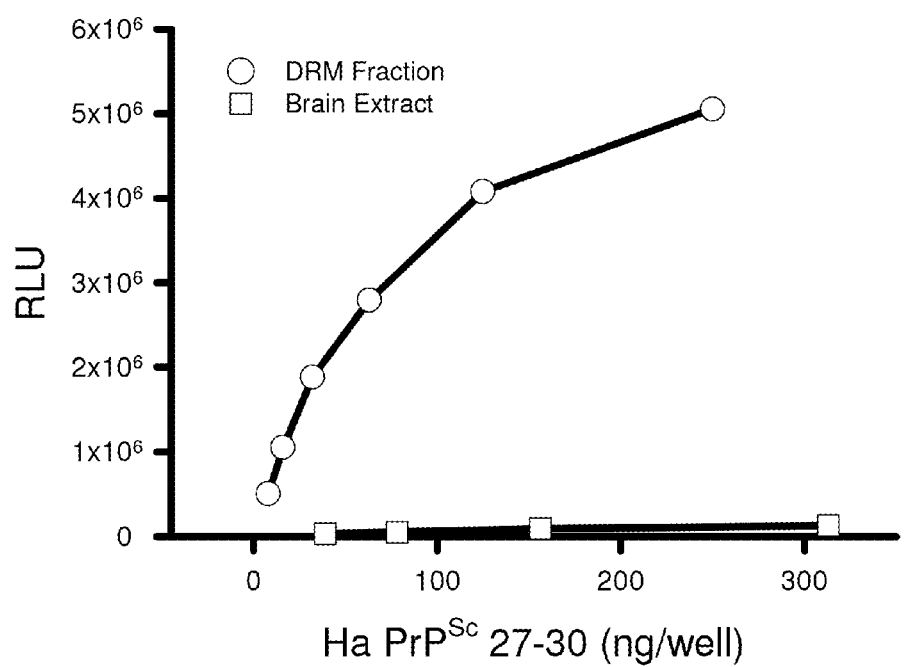
FIG. 12 is a plot that compares detection of prion from hamster brain extract (squares) to brain DRM (circles) by ELISA. Enhanced detection (~50 fold) of Proteinase-K resistant prion (Ha PrP$^{Sc}$ 27-30) from DRM fractions compared to crude brain with DRM1-31 anti-prion monoclonal antibody.
Figure 13:
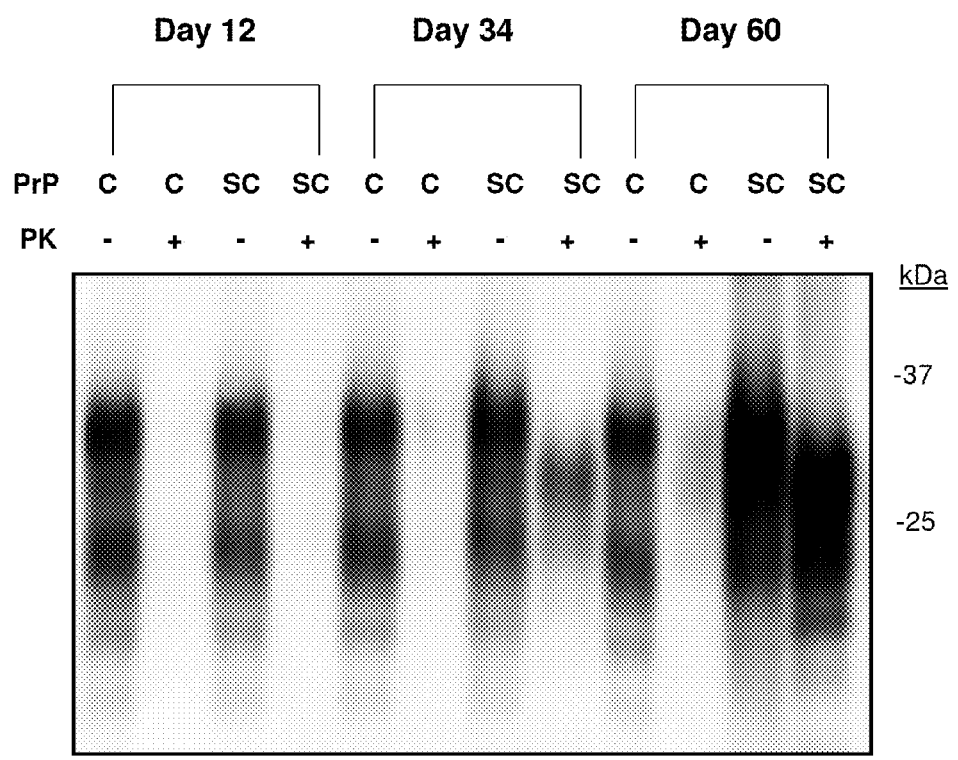
FIG. 13 is a Western blot showing preclinical detection of PK-resistant prion protein in hamster brain DRM fractions by day 34 post-infection with monoclonal anti-prion DRM1-31 antibody. Prion detection at day 34 is ~30 prior to onset of clinical prion symptoms.
Figure 14:
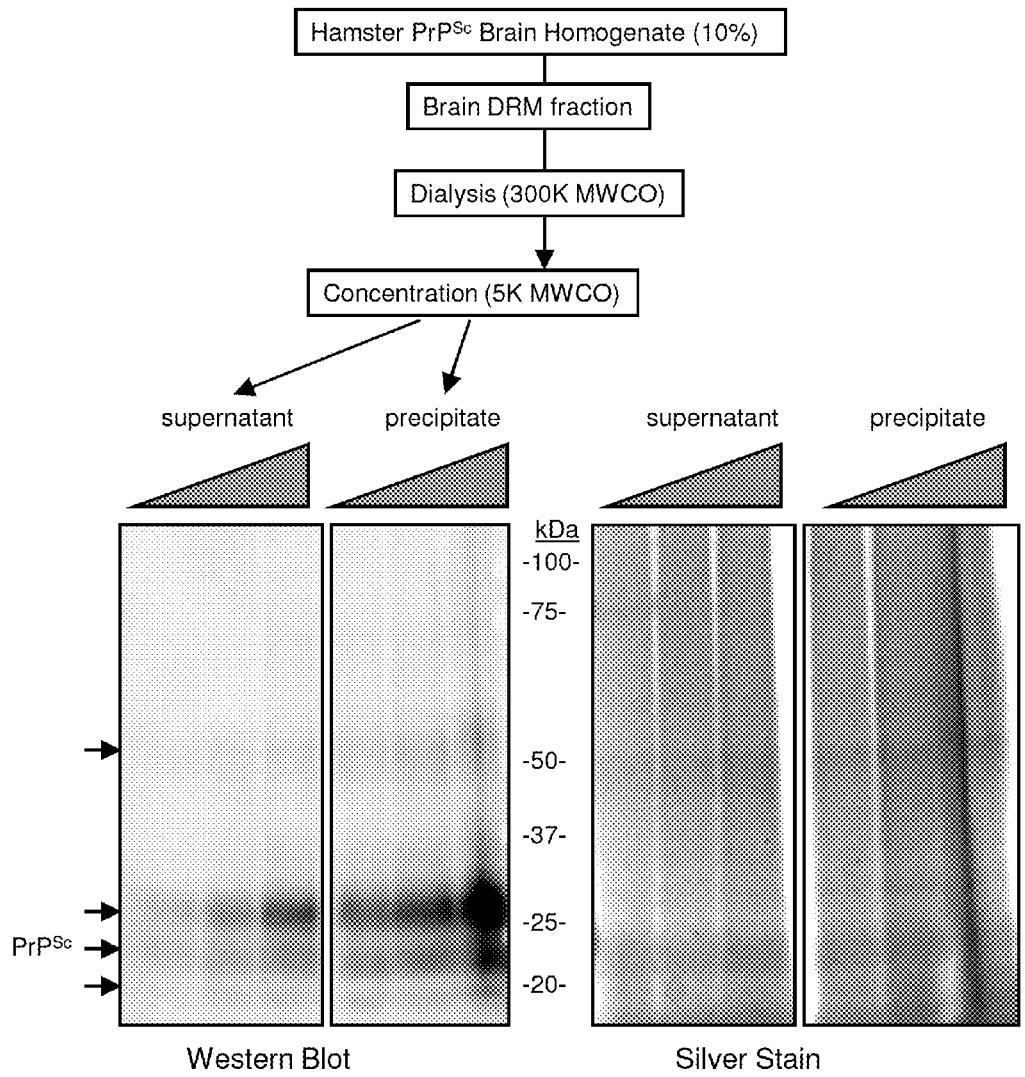
FIG. 14 is a photo of the detection of prion (PrP$^{Sc}$) by SDS-PAGE Western blot and silver stain following dialysis (>300 kDa MWCO) and concentration by centrifugation (5 kDa MWCO) of prion infected hamster brain detergent resistant membranes (DRM).

The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement.

Herein is described a novel method to purify infectious prion from biological tissue and fluids wherein the purified prion serves as inoculums for antibody generation or target of detection. The purification and enrichment of prion proceeds through (a) Prion isolation with detergent resistant membranes (DRM), (b) Proteinase-K (PK) enzymatic treatment and phosphotungstic acid (PTA) protein precipitation and (c) Size exclusion chromatography and PTA concentration. Alternatively, the purification and enrichment of prion proceeds through (a) Prion isolation with detergent resistant membranes (DRM), (b) dialysis with >300 kDa molecular weight cut-off (MWCO), (c) protein concentration. Post-translational processing of $PrP^C$ includes the addition of a GPI-anchor that targets the protein to lipid rafts of the plasma membrane (31;32). This localization is important for the conformational conversion of $PrP^C$ into infectious prion (33-36). Biochemically these lipid-rich membrane domains can be isolated by sucrose density centrifugation as buoyant detergent resistant membranes (DRMs) containing both $PrP^C$ and $PrP^{Sc}$ proteins (10;31). Exploitation of this methodology allows for a significant enrichment and purification, effectively separating >99% of brain protein from prion in a single step. The resulting DRM fraction is enriched in $PrP^{Sc}$ (>40-fold) relative to crude brain homogenate and represents <1% total brain proteins. Prions in the DRM fraction remain soluble and are highly infectious in bioassay. Treatment of DRM fractions with PK effectively removes $PrP^C$ and results in $PrP^{Sc}$ truncation to form PrP 27-30. Abnormal infectious prions (PrPSc) form large molecular weight aggregates that differ from normal PrPC and dialysis with high molecular weight cut-off can be used to separate aggregate PrPSc from PrPC.

Phosphotungstic acid (PTA) has been used effectively to precipitate prion protein (37;38). The application of PTA to precipitate $PrP^{Sc}$ after PK-digestion from DRMs provides an effective method to both concentrate and separate prion from lipids in the enriched DRM preparation. In addition, we found $PrP^{Sc}$ in brain DRM fractions is highly aggregated with a molecular mass of >400 kDa. We exploited this property by using size exclusion chromatography to further separate $PrP^{Sc}$ from residual PK (<30 kDa) and other protein fragments. Chromatography over Sephadex G100 allowed us to rapidly collect the majority of $PrP^{Sc}$ in the column void fraction while residual proteins <100 kDa were retarded by the gel. The resulting $PrP^{Sc}$ fraction ($PrP^{Sc}$ DRM-PK-PTA-G100) retained infectivity as determined in bioassay. The $PrP^{Sc}$ fractions from multiple column separations were pooled and concentrated by a second PTA precipitation to yield a highly purified $PrP^{Sc}$ pellet ($PrP^{Sc}$ DRM-PK-PTA-G100-PTA). This method (outlined in FIG. 6) allowed for sufficient accumulation of $PrP^{Sc}$ devoid of endogenous $PrP^C$ and other contaminating proteins to yield a Coomassie stainable band of the correct molecular mass that corresponded to $PrP^{Sc}$ by Western blot.

An additional embodiment of the aforementioned method is non PK based using dialysis with a high molecular weight cut off after prion isolation with DRM. Dialysis with high molecular weight cutoff (HMWCO), greater than 300 kDa, of biological samples can be used in the diagnostic detection of diseases associated with protein aggregation, such as transmissible spongiform encephalopathies, Alzheimer's and Parkinson's. Dialysis with HMWCO can be used with protein concentration methods Dialysis with HMWCO can be used with protein concentration methods, such as PTA and centrifuge with concentration by small MWCO membranes, to enhance detection of abnormal aggregate proteins such as prions, Tau, β-amyloid, Synuclein and other aggregate proteins associated with disease as part of diagnostic detection assays. Dialysis with HMWCO can be used to concentrate and remove infectious prions or other aggregate proteins from environmental and biological samples and can be used to concentrate and separate full-length infectious ($PrP^{Sc}$) from normal native ($PrP^{C}$) prion from biological samples blood, urine, and tissue extracts for enhanced detection and disease diagnosis. Dialysis with HMWCO can be used to concentrate and separate aggregate forms of disease associated proteins from non-aggregate normal counterparts for enhanced detection and disease diagnosis. HMWCO combined with prion enrichment methods can be used to isolate full-length infectious prion ($PrP^{Sc}$) aggregates for biochemical analysis such as immunogen preparation, structural analysis, the identification of prion-binding compounds, the identification of amino acid modifications, and disease infectivity).

An embodiment of the invention is the generation of Prnp-null Balb/c JAX and Balb/c Bailey mice wherein the Balb/c Bailey strain is useful for generation of a prion ablated myeloma cell line that can be used as a hybridoma fusion partner resulting in novel hybridomas producing monoclonal anti-prion antibodies. The mice would provide a molecular genetic tool for selective prion immuno-response. Additionally, wild-type mice from different genetic backgrounds could provide a suitable host for immunization with the described purified prion immunogen and hybridoma selection screen for the generation of anti-prion antibodies.

The development of a $Prnp^{0/0}$/Balbc/J mouse provides a useful genetic background to promote a robust immune response to prions and production of monoclonal antibodies. These mice offer a syngenic background for myeloma-spleenocyte fusion and subsequent hybridoma generation. Indeed, our data shows that despite the purity of our prion inoculum it serves as a poor immunogen in wt Balb/cJ mice. However, the lack of detection of any other brain DRM proteins using the antisera from immunized wt Balbc/J mice supports the purity of our prion inoculum. In sharp contrast, immunization of $Prnp^{0/0}$/Balb/cJ mice elicits a robust immune response that resulted in production of high-titer anti-prion specific antiserum. The response appears comparable by Western blot to that observed with established monoclonal anti-PrP antibodies. Additionally, no antibodies against other brain DRM proteins were detected in the antisera from these mice again suggesting a highly purified inoculum.

Antisera from the $Prnp^{0/0}$/Balb/cJ mice recognized both PK-sensitive and -resistant PrP proteins. However, the model outlined here is well suited for the generation of hybridomas and isolation of monoclonal antibodies. Herein is described a method for the enrichment of infectious prions from lipid rafts and their subsequent purification in sufficient quantity to elicit a robust and selective immune response in $Prnp^{0/0}$/Balb/cJ mice.

The robust immune response of $Prnp^{0/0}$/Balb/cJ mice to purified prion immunogen resulted in selective high-titer anti-prion antisera. Hybridoma technology combined with comparative screening was effective in isolating cells that produce only anti-prion monoclonal antibodies. These DRM antibodies show high-affinity and selectivity for prion protein and are useful for immunoassay detection of infectious prions by ELISA and Western blot. Moreover, combined with prion enrichment in detergent resistant membranes we could detect prions in asymptomatic animals as early as 34 days post infection by Western blot.

Another embodiment of the invention is a method of identifying hybridoma cells producing prion specific antibodies using differential comparative direct binding ELISA for antibody screening and selection. The hybridoma selection and use of detergent resistant membrane binding assay proceeds through (a) a primary screen of hybridoma conditioned media on prion containing PK-treated brain derived DRMs ($PrP^{Sc}$ DRM+PK). Positive binders are indicated by greater than 3-fold above background selected and (b) a secondary screen of select hybridomas by comparative binding against infectious and normal (PrP) as well as $PrP^{C}$ and $PrP^{Sc}$ plus and minus PK treatment and recombinant derived PrP peptide. The binding phenotype of putative anti-$PrP^{Sc}$ monoclonal antibodies are as follows: (+)$PrP^{Sc}$ DRM, (+) $PrP^{Sc}$DRM+PK, (−) $PrP^{C}$ DRM, (−) $PrP^{C}$ DRM+PK, (−) recombinant PrP protein, (−) proteinase-K. Combinations of the antigens listed above can be used during different phases of the screening strategy for selection of hybridomas producing anti-prion monoclonal antibodies.

A further embodiment of the invention is the generation of prion specific antisera, hybridomas and monoclonal antibodies via immunization of animals with purified prion derived from DRM fractions as well as the generation of a hybridoma cell lines producing anti-prion monoclonal antibodies. Three hybridoma cell lines have been cloned, monoclonal anti-prion antibodies isolated, and binding epitopes to prion proteins defined. Hybridoma cell lines making anti-prion monoclonal antibodies include: 1) DRM1-31 which binds a discontinuous epitope corresponding to amino acids 159-170 (NQVYYRPVDQYN), SEQ ID NO:1 and 215-226 (CTTQYQKESQAY), SEQ ID NO:2 of the Ha PrP protein sequence; 2) DRM1-60 which binds to amino acids 159-170 (NQVYYRPNDQYN), SEQ ID NO:3 corresponding to Ha PrP protein sequence; and 3) DRM2-118 which binds to amino acids 88-92 (GWGQGG), SEQ ID NO:4 corresponding to Ha PrP protein sequence.

Methods for diagnostic detection of prion diseases in environmental or biological samples using DRM prion enrichment and/or generated anti-prion antibodies. A significant enrichment of prion concentration in biological or environmental samples would aid in detection of infectious prions by immunoassay or other diagnostic approaches. Prions localized in DRM fractions provide novel source of infectious prions as target for detection, antibody screening, source of inoculum for antibody generation.

Methods for therapeutic intervention in prion diseases using identified monoclonal anti-prion antibodies. Humanized monoclonal anti-prion antibodies can be infused in patients with prion diseases as a therapeutic treatment.

EXAMPLES/PROCEDURES

Animals

All animals were housed in pairs on a 12 h light-dark cycle and provided continual access to food and water. All protocols were approved by the USDA animal care and use committee and experimental procedures conducted in certified BL2 laboratory. Hamster-passaged Sc237 scrapie prions were propagated in female Syrian Golden hamsters (LVG; Charles Rivers Laboratory, MA) beginning at 4 weeks of age. Prion-infected hamsters were sacrificed when clinical symptoms included; increased startle response, ataxia, and >5s righting reflex. Prnp$^{0/0}$/Balb/cJ mice were generated at the University of California, San Francisco under approved animal protocols by speed congenic backcrossing 129/SvJ/ C57-BL6 Prnp$^{0/0}$ to inbred Balb/cJ mice and homozygosity verified by PCR as previously described (14;18). Antisera was obtained from anesthetized mice following transcardiac puncture with a 20-gauge needle attached to a 3 mL syringe, transferred to a BD Vacutainer SST tube (BD Biosciences), allowed to clot and sera collected after centrifugation.

Inoculation

Infectious PrP$^{Sc}$ was propagated by serial passage in hamster brain following 40 µL intracerebral inoculation of a 1% brain homogenate in 320 mM sucrose using a 27-gauge needle inserted into the right parietal lobe. Detergent resistant membrane (DRM) fractions were diluted in sucrose to a final concentration of 320 mM and inoculated as described. Phosphotungstic acid (PTA) precipitated protein pellets were solubalized in n-octyl-glucoside to final concentration of 60 mM, diluted in sucrose and inoculated as described. Incubation time assay was used to calculate ID$_{50}$ using the equation Log T=17+[Log D]−(0.138*Y) and used for calculation of specific infectivity (ID$_{50}$/mg inoculum). Onset of clinical scrapie was determined by occurrence of two symptoms in days post-inoculation as defined above. Prnp$^{0/0}$/Balb/cJ mice starting at 25d were inoculated (i.p.) with 100 µL antigen using the following regime: two inoculations containing purified PrP$^{Sc}$ in RIBI adjuvant (Sigma-Aldrich, MO; Sigma Adjuvant System) separated by 10 days. Sera was collected 3 days after the final inoculation and evaluated for anti-PrP immunoreactivity.

Reagents

All reagents were of the highest grades commercially available. All antibodies were diluted in 10 mM Tris Buffered Saline with 1% Tween-20 (TBST) containing 1% IgG-free BSA (Jackson Immuno Chemical, PA). Primary antibodies used include: Caveolin-1 rabbit polyclonal diluted 1:1K (Santa Cruz, Calif.; N20), Flotillin-1 rabbit polyclonal diluted 1:1K (Santa Cruz; H-104), IPC1 anti-prion monoclonal diluted 1:10K (Sigma). Secondary antibodies include: goat-anti-mouse-HRP and goat-anti-rabbit-HRP diluted 1:10K (Pierce, Ill.). Recombinant Syrian hamster (recSHa) PrP(90-231) was generated at UCSF as previously described (19).

Isolation of Detergent Resistant Membranes

Hamster brains were homogenized (10% w/v) on ice in 25 mM MES (pH 6.5) with 150 mM NaCL, 1% Triton X-100, 60 mM n-octyl-glucoside, 10 mM PMSF, and protease inhibitors (Complete mini; Roche, C H). The homogenate was pre-cleared by centrifugation (1000×g) at 4° C. and supernatant mixed with equal volume of 80% sucrose in 25 mM MES (pH 6.5) with 150 mM NaCL. A 12 mL discontinuous sucrose gradient was formed by applying 4 mL of the 40% brain-sucrose in the bottom of a clear ultra-centrifuge tube (14×89 mm; Beckman, Calif.) followed by a 4 mL layer of 30% MES-Sucrose then 4 mL 5% MES-Sucrose. Tubes were placed in a SW-40T rotor and centrifuged at 39,000 RPM at 4° C. for 18 h in a L8-70M class H ultra-centrifuge (Beckman). A visible lipid-rich band corresponding to the detergent resistant membrane (DRM) fraction was observed within the 30-5% sucrose zone and collected (~1 mL/gradient).

Linear Sucrose Sedimentation Gradient

DRM fractions obtained from hamster brain homogenates were mixed with n-octyl-glucoside to a final concentration of 60 mM and incubated at 4° C. for 15 min with rotation. A cushion of 250 µL of 50% sucrose in 25 mM MES (pH 6.5) with 150 mM NaCL and 60 mM n-octyl-glucoside was place in the bottom a clear ultra-centrifuge tubes (11×60 mm; Beckman) and a 50-5% linear sucrose gradient (4 mL) formed using a mixing gradient maker. The DRM fraction was loaded (300 µL) to the top of the gradient and tubes centrifuged in a SW60 rotor at 50,000 RPM for 10 h at 4° C. in a L8-70M class H ultra-centrifuge. 12×0.35 mL fractions were collected and analyzed. The gradient was calibrated with known molecular standards as previously described (20).

Western Blotting

Protein concentration was quantified using a micro-BCA assay (Pierce). Proteinase-K (PK; Roche) treatment was used at a final concentration of 25 µg/mL for brain homogenates and 150 µg/mL for DRM fractions for 1 h at 60° C. and inactivation of PK was by denaturation in LDS sample buffer or by addition of PMSF to 10 mM. Electrophoresis was performed on heat denatured samples in LDS buffer normalized by BCA and loaded on 4-12% Bis-Tris gels electrophoresed with MOPS running buffer (Novex; Invitrogen). Gels were transferred to nitrocellulose (Bio-Rad), washed in TBST, blocked with 10% non-fat dry milk, probed with antibodies, protein bands resolved by ECL (Supersignal; Pierce) and imaged on a Flurochem HD documentation system (Alpha Innotech, Calif.). Gel staining was performed with Coomassie blue (R250; Sigma) or Silver (ProteoSilver Plus; Sigma) and imaged on a light box.

Direct ELISA

Samples with equivalent protein concentration were diluted in 0.1 M sodium bicarbonate buffer (pH 9.4) and 100 µL absorbed to 96-well maxisorb plates (NUNC, NY) overnight at 4° C. Plates were washed in TBST, blocked in 10% non-fat milk for 1 h at 37° C., incubated 1 h with primary antibody, washed, incubated 1 h with HRP-conjugated secondary antibody, washed, resolved by chemiluminescence (Supersignal; Pierce) detection using Victor$^2$ plate reader (PerkinElmer, MA) and expressed as relative light units (RLU).

Phosphotungstic Acid Protein Precipitation (PTA)

A stock of sodium phosphotungstate hydrate (Aldrich, Wis.) was dissolved at 4% in PBS (pH 7.4) with 170 mM MgCl$_2$. PTA was added to samples to a final concentration of 0.3% with 13 mM MgCL$_2$ and incubated at room temperature for 10 min. Precipitated protein was centrifuged at 10,000×g for 20 min at 4° C., pellets washed repeatedly with 200 mM EDTA in PBS followed by centrifugation with a final wash in ddH$_2$O with remaining water aspirated after centrifugation. PTA pellets were solubalized with n-octyl-glucoside to a final concentration of 60 mM in buffer.

Size Exclusion Chromatography

A 15 mL gel bed of Sephadex G100 (Superfine grade, Sigma) was poured in a glass column and equilibrated in 25 mM Tris-HCL (pH 7.4). Column calibration was performed with gel filtration standards (Bio-Rad, CA; #151-1901) and samples loaded at 250 µL in 25 mM Tris-HCL (pH 7.4) with 60 mM n-octyl-glucoside. Proteins were fractionated with 25 mM Tris-HCL (pH 7.4) at a flow rate of 100 µL/min in 1 mL fractions. Column void was defined at 5 mL with detectable high molecular weight standards (>100 kDa) eluted.

Differential Hybridoma Screen

Figure 15:
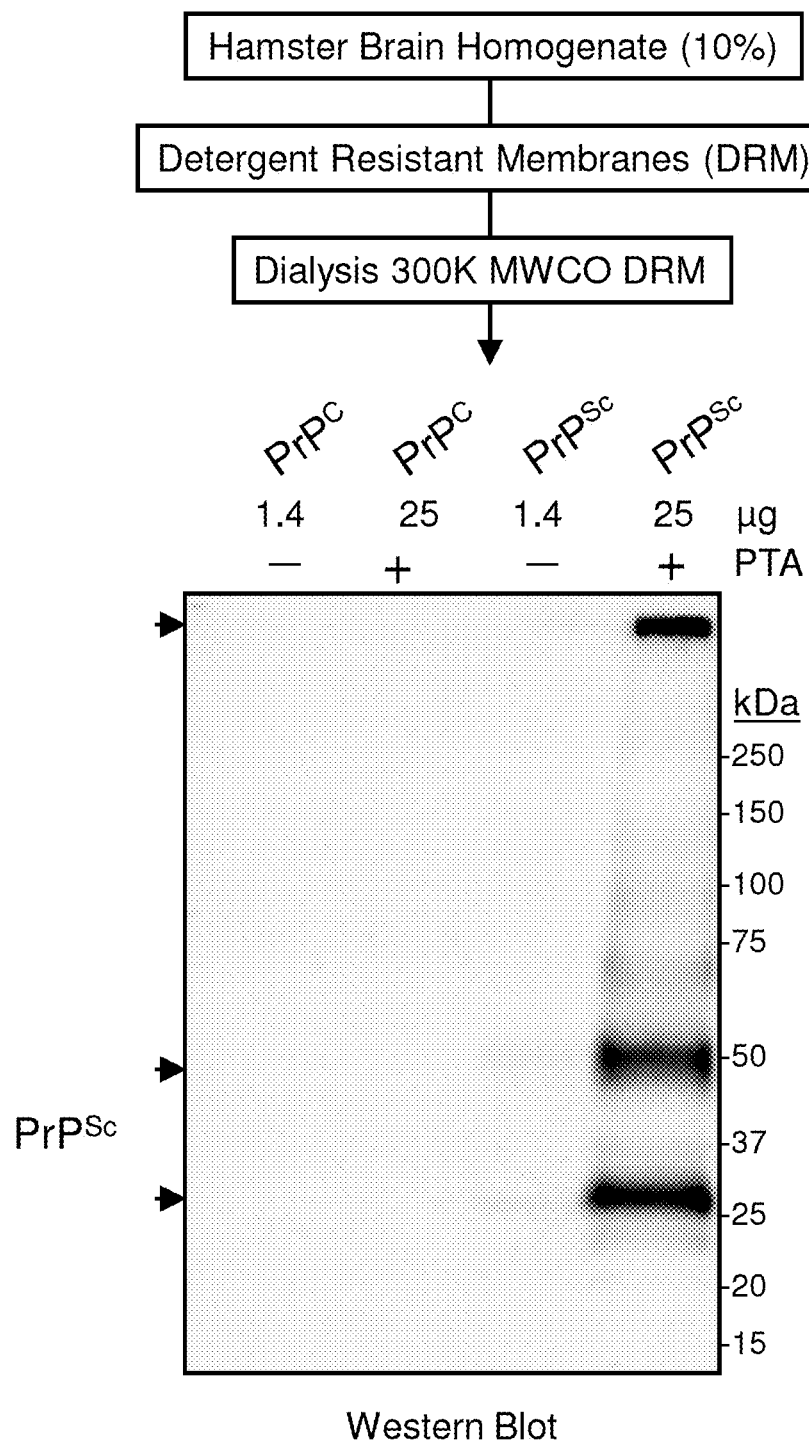
FIG. 15 is a photo of the detection of abnormal ($^{Pr}P^{Sc}$), but not normal (PrP$_C$) prion protein, following dialysis (>300 kDa MWCO) of brain detergent resistant membranes (DRM).

Following immunization of animals with a purified prion brain DRM derived prion preparation and spleenocyte-myeloma fusion resulting hybridomas are sequentially screen by comparison of supernatant binding to normal PrP$^C$ and PrP$^{Sc}$ proteins. To monoclonal antibodies that selectively bind to the infectious prion isoform an initial screen of hybridoma supernatant binding to proteinase-K treated prion infected brain DRM fractions on a microtiter plate is evaluated. Hybridomas that bind to PK-resistant prion in brain DRM fractions are expanded then supernatant is evaluated in a secondary screen for binding activity to $PrP^C$, $PrP^{Sc}$+PK and recombinant PrP. Those that bind all three antigens are producing anti-prion monoclonal antibody that is not selective but recognizes both the $PrP^{C}$ and $PrP^{Sc}$ isoforms. Those that bind on the $PrP^{Sc}$+PK antigen are producing prion selective monoclonal antibody that recognizes only the infectious PK-resistant PrPSc isoform.

Hybridoma Cell Cloning and Antibody Purification

Hybridoma cells were isolated by limiting dilution and clones expanded for monoclonal antibody production. Cloned hybridoma cells are inoculated into mice and ascites obtained and purified by protein-G affinity chromatography. Five anti-prion monoclonal antibodies were identified and assigned the designation DRM. All antibodies identified specifically recognized prion proteins, three of these antibodies; DRM1-31 (Ha PrP amino acids 159-170 (NQVYYRPVDQYN), SEQ ID NO:1 and 215-226 (CTTQYQKESQAY), SEQ ID NO:2, DRM1-60 (Ha PrP amino acids 159-170 (NQVYYRPNDQYN), SEQ ID NO:3, DRM2-118 (Ha PrP amino acids 88-92 (GWGQGG), SEQ ID NO:4 were shown to have distinct genetic sequences in their IgG domain variable region.

Results

Prion Isolation with Detergent Resistant Membranes

A sucrose density gradient effectively separates soluble proteins from those that are detergent resistant at 4° C. by exploiting differences in buoyancy properties due to lipid-association of some proteins. A measure of total protein following fractionation of crude brain homogenate (12×1 mL) showed that the majority of proteins (>99%) were retained at the bottom of the sucrose gradient between fractions #8-12 (40% sucrose), whereas a small protein peak (<1%) migrated to the zone of the 5/30% sucrose in fractions #4-5 corresponding to detergent resistant membrane (DRM) derived from lipid rafts (FIG. 1A). Western blots of the gradient fractions from normal and diseased hamster brain reveals that the most of the $PrP^{C}$ (FIG. 1B; top left panel) and $PrP^{Sc}$ (FIG. 1B; top right panel) were found in the DRM fraction #4 of the minor protein peak. As a positive control for DRM proteins, Flotillin-1, a known lipid raft protein, was detected by Western blotting from the same gradient fractions and localized as expected to DRM fraction #4 (FIG. 1B; bottom panels). Aliquots of each gradient fraction were used as antigen in a direct binding ELISA for detection of PrP protein. Confirming the Western blots, the majority of $PrP^{C}$ from normal brain (FIG. 1C; left panel) and $PrP^{Sc}$ from diseased brain (FIG. 1C; right panel) were localized in the DRM-enriched fraction #4.

Prion Enrichment

Prion enrichment was evaluated by comparing levels of PK-resistant $PrP^{Sc}$ in crude brain homogenate to DRM gradient fractions. At equal concentration of total protein the DRM fraction contained ~50-fold more detectable prion relative to crude brain homogenate by direct ELISA (FIG. 2A, FIG. 12; t-test P<0.001). Prion enrichment in DRM was further evaluated by Western blot with a detectable increase in band intensity for all three $PrP^{Sc}$ glycoforms in DRM fractions relative to crude brain homogenates (FIG. 2B). PTA precipitation of DRM fractions resulted in increased prion detection relative to the DRM fraction alone.

Prion in DRM is High Molecular Weight

FIG. 3 compares the oligomeric status of the PrP found in normal and scrapie enriched DRM preparations from brain homogenates. The DRM fractions were subjected to sedimentation gradient centrifugation in a linear sucrose gradient. Each gradient was then fractionated into 12 equal fractions and each fraction evaluated by Western blot probing with anti-PrP antibody (FIG. 3; top panel), anti-Caveolin-1 antibody (FIG. 3; middle panel), and anti-Flotillin-1 antibody (FIG. 3; bottom panel). $PrP^{C}$ in the DRM from normal brain resides as monomeric to high molecular weight aggregate with the detection of mono- and di-glycosylated isoforms predominant (FIG. 3; top left panel). In contrast, the $PrP^{Sc}$ in the DRM from diseased brain was observed as high molecular weight aggregate >400 kDa dominated by the mono- and di-glycosylated isoforms (FIG. 3; top right panel). Moreover, non-glycosylated PrP was readily detectable across the gradient at varied molecular weights in DRMs from prion infected brain, yet this isoform was PK-sensitive (FIG. 3; bottom right panel) suggesting detection of $PrP^{C}$. Caveolin-1 and Flotillin-1, established lipid raft proteins (20), were used as markers to validate the integrity of the gradients and were detected as high molecular weight oligomers (FIG. 3; bottom left panels).

Isolation of Prion Protein

Limited PK-digestion of $PrP^{Sc}$ positive DRM fractions resulted in the proteolytic degradation of $PrP^{C}$ and the N-terminal truncation of $PrP^{Sc}$ to form PrP 27-30. Importantly, the PK-digested samples also included peptide fragments, PK, and lipids. To isolate $PrP^{Sc}$ from these contaminants, we exploited preferential binding and precipitation of $PrP^{Sc}$ by PTA. Following PK-digestion of $PrP^{Sc}$ DRM fraction, proteins were PTA precipitated then solubilized and fractionated over Sephadex G100. A major protein peak emerged at the column void fraction #5 (void >100 kDa; FIG. 4A; top panel; solid line) where $PrP^{Sc}$ was detected by ELISA (FIG. 4A; top panel; dashed line). Evaluation of eluted G100 fractions by Western blot shows that the majority of $PrP^{Sc}$ was detected in the void fraction #5 (FIG. 4B). FIG. 4C shows that $PrP^{Sc}$ was further concentrated by a second PTA precipitation after elution from G100 (FIG. 4C). Electrophoresis of the PTA concentrated G100 eluted fraction #5 followed by silver (FIG. 4D; left panel) and Coomassie blue staining (FIG. 4D; middle panel) revealed proteins at the correct molecular mass corresponding to $PrP^{Sc}$ detected by Western blot (FIG. 4D; right panel).

Purified Prion Retains Infectivity

Using the hamster bioassay we showed that the DRM fraction ($PrP^{Sc}$ DRM) isolated from prion-infected brain homogenate remained infectious (FIG. 5A). Likewise, the purified PK-resistant $PrP^{Sc}$ from DRM fractions that had been PTA precipitated and fractionated over Sephadex G100 ($PrP^{Sc}$ DRM-PK-PTA-G100) retained infectivity (FIG. 5A). Our purification scheme resulted in a progressive increase in both the $ID^{50}$ and a >20-fold, and >40-fold increase in specific infectivity of DRM fractions and purified DRM (PrPSc DRM-PK-PTA-G100) relative to 1% crude brain homogenate, respectively (FIG. 5B).

Dialysis with High Molecular Weight Cut Off—Detection of Abnormal ($^{Pr}P^{Sc}$)

Normal and prion infected hamster brains were homogenized, detergent resistant membranes (DRM) isolated, dialyzed against water using a 300 kDa molecular weight cut off (>300K MWCO), and dilute fraction (−) or phosphotungstic acid (PTA) concentrate (+) were evaluated by SDS-PAGE Western blot using anti-prion monoclonal antibody DRM2-118 (1 μg/mL) with chemiluminescent detection. At equivalent protein concentration only prion infected hamster brain had detectable prion protein. Native non-aggregate PrP$^C$ protein was effectively dialyzed out of the DRM fraction, whereas the high molecular weight aggregate PrP$^{Sc}$ (see FIG. 15) was retained by a 300 kDa MWCO. Protein precipitation of dialyzed DRM fraction with PTA effectively concentrated detectable prion protein. This figure demonstrates a diagnostic immunoassay that uses non-enzymatic removal of native PrP$^C$ to detect abnormal PrP$^{Sc}$ capable of discriminating normal from prion infected sample.

Dialysis with high molecular weight cutoff (>300K MWCO) of brain DRM fraction followed by sample concentration by centrifugation through 5 kDa MWCO filter effectively retains infectious PrP$^{Sc}$ protein. 5K MWCO concentration results in a supernatant and protein precipitate. PrP$^{Sc}$ protein was detectable in both the supernatant and precipitate fraction by Western blot using DRM1-31-HRP (1 μg/mL) at 5, 10, 20 μg/well (◄) by chemiluminescence. Silver stained protein bands were observed in the gel following SDS-PAGE corresponding to $PrP^{Sc}$ detected by Western blot. See FIG. 14.

Purified $PrP^{Sc}$ is Immunogenic in $Prnp^{0/0}$/Balb/cJ Mice $Prnp^{0/0}$/Balb/cJ mice were immunized with a $PrP^{Sc}$ fraction enriched for prion infectivity according to the purification scheme outlined in FIG. 6. Antisera from $PrP^{Sc}$ immunized $Prnp^{0/0}$/Balb/cJ mice (#1-2) bound recombinant Syrian hamster (recSHa) PrP(90-231) at an end-point dilution >1:30000 by ELISA (FIG. 7A). No SHa PrP(90-231) binding was observed using sera from immunized wt Balb/cJ mice (#3-4). Western slot-blot experiments compared binding of antisera from immunized $Prnp^{0/0}$/Balb/cJ mice #1-2 and wt Balb/cJ mice #3-4 (FIG. 7B) to recSHaPrP(90-231), $SHaPrP^{Sc}$ DRM without limited PK-digestion ($PrP^C$ plus $PrP^{Sc}$), and ShaPrP 27-30 in DRMs. Antisera from immunized $Prnp^{0/0}$/Balb/cJ mice was effective in detecting both $PrP^C$ and $PrP^{Sc}$ proteins at dilutions >25 K. In contrast, antisera from immunized wt Balb/cJ mice did not detect PrP proteins at any dilution tested. The lack of immunoreactive sera from immunized wt Balb/cJ mice to other DRM proteins further supports the purity of the prion inoculum and lack of immunogenicity of the $PrP^{Sc}$ protein in wt animals.

Further characterization of antisera binding to protein in crude brain homogenate and brain-derived DRM fractions from normal ($PrP^C$) and disease ($PrP^{Sc}$) hamster brain with (+) and without (−) PK-digestion is shown from a representative immunized $Prnp^{0/0}$/Balb/cJ mouse by Western blot (FIG. 8; top panel). Weak binding to $PrP^C$ was observed in normal brain homogenate (30 μg/lane) compared to the strong binding to $PrP^C$ from enriched DRM (10 μg/lane) preparation (FIG. 8, $PrP^C$; arrow). Limited PK-digestion of normal brain samples resulted in the complete loss of detectable $PrP^C$ using the antisera. Strong binding to $PrP^{Sc}$ was observed in both crude brain homogenates and DRM preparations from disease brain with detection of PrP 27-30 at the expected molecular mass. Importantly, antisera from immunized $Prnp^{0/0}$/Balb/cJ mice only detected PrP proteins. As a control, a companion blot was probed with the anti-PrP monoclonal antibody IPC1 (FIG. 8; bottom panel). A similar pattern of binding to $PrP^C$ and $PrP^{Sc}$ was observed with IPC1 as compared to the antisera from immunized $Prnp^{0/0}$/Balb/cJ mice.

Spleenocytes from prion immunized $Prnp^{0/0}$/Balb/cJ mice were fused with myeloma cells and hybridomas screened for anti-prion monoclonal antibody production. Hybridoma cells making anti-prion monoclonal antibodies were identified and cells cloned by limiting dilution. Five hybridoma clones were selected for ascites production in mice and resulting DRM antibodies purified by protein-G affinity chromatography. Anti-prion monoclonal antibodies were characterized by ELISA and Western blot and shown to bind with high affinity to proteinase-K resistant prion protein in hamster brain DRM (FIG. 9). Further characterization revealed different binding affinities of DRM antibodies to multiple recombinant PrP species. All monoclonals bound with near equal affinity recombinant hamster PrP, whereas DRM1-60-6-2 and DRM2-118-9-4 bound ovine and human rec PrP with high affinity, respectively (FIG. 10). Differences in species specificity for endogenous brain PrP was also observed by Western blot, with DRM1-31 showing strong binding to hamster and cervid PrP only. DRM1-60 and DRM2-118 showed broad species specificity (FIG. 11). Infected hamster brain DRM fractions were evaluated by Western blot with the DRM1-31 monoclonal antibody at 12, 34, and 60 days post prion infection. Prion infected animals at these time points are asymptomatic. The Western blot shows that DRM1-31 can detect PK-resistant prion as early as 34 days after infection, ~30 before clinical symptoms appear.

What is claimed:

1. An isolated and purified monoclonal antibody produced by the continuous hybridoma cell line of DRM1-31.

2. A composition comprising the monoclonal antibody of claim 1.

3. An isolated and purified monoclonal antibody produced by the continuous hybridoma cell line of DRM1-60.

4. A composition comprising the monoclonal antibody of claim 3.

5. An isolated and purified monoclonal antibody produced by the continuous hybridomna cell line of DRM2-118.

6. A composition comprising the monoclonal antibody of claim 5.

7. A kit for detecting prion epitopes in a sample, said kit comprising: (1) a container comprising an isolated and purified monoclonal antibody produced by the continuous hybridoma cell line DRM1-31, DRM1-60, DRM2-118 or mixtures thereof; (2) instructions for using the antibody for the purpose of binding to prion epitope to form an immunological complex; and (3) instructions for detecting the formation of the immunological complex such that presence or absence of immunological complex correlates with the presence or absence of prion epitope in said sample.

8. A method for detecting epitopes of prions comprising (1) incubating a sample with an isolated and purified monoclonal antibody produced by the continuous hybridoma cell line DRM1-31, DRM1-60, DRM2-118, or mixtures thereof under conditions allowing antibody-prion epitope complex to form; and (2) detecting the antibody-prion epitope complex wherein the presence or absence of the complex indicates the presence or absence of prion epitope in the sample.

* * * * *

SEQUENCE LISTING

```
<160> NUMBER OF SEQ ID NOS: 4

<210> SEQ ID NO 1
<211> LENGTH: 12
<212> TYPE: PRT
<213> ORGANISM: Unknown
<220> FEATURE:
<223> OTHER INFORMATION: DRM1 31

<400> SEQUENCE: 1

Asn Gln Val Tyr Tyr Arg Pro Val Asp Gln Tyr Asn
1               5                   10

<210> SEQ ID NO 2
<211> LENGTH: 12
<212> TYPE: PRT
<213> ORGANISM: Unknown
<220> FEATURE:
<223> OTHER INFORMATION: DRM1 31
```

-continued

```
<400> SEQUENCE: 2

Cys Thr Thr Gln Tyr Gln Lys Glu Ser Gln Ala Tyr
1               5                   10

<210> SEQ ID NO 3
<211> LENGTH: 12
<212> TYPE: PRT
<213> ORGANISM: Unknown
<220> FEATURE:
<223> OTHER INFORMATION: DRM1 60

<400> SEQUENCE: 3

Asn Gln Val Tyr Tyr Arg Pro Asn Asp Gln Tyr Asn
1               5                   10

<210> SEQ ID NO 4
<211> LENGTH: 6
<212> TYPE: PRT
<213> ORGANISM: Unknown
<220> FEATURE:
<223> OTHER INFORMATION: DRM2 118

<400> SEQUENCE: 4

Gly Trp Gly Gln Gly Gly
1               5
```